United States Patent
Lu et al.

(10) Patent No.: US 8,022,216 B2
(45) Date of Patent: Sep. 20, 2011

(54) MALEATE SALTS OF (E)-N-{4-[3-CHLORO-4-(2-PYRIDINYLMETHOXY)ANILINO]-3-CYANO-7-ETHOXY-6-QUINOLINYL}-4-(DIMETHYLAMINO)-2-BUTENAMIDE AND CRYSTALLINE FORMS THEREOF

(75) Inventors: Qinghong Lu, Suffern, NY (US); Mannching Sherry Ku, Thiells, NY (US); Warren Chew, Pierrefonds (CA); Gloria Cheal, Beaconsfield (CA); Anthony F. Hadfield, St. Petersburg, FL (US); Mahmoud Mirmehrabi, Laval (CA)

(73) Assignee: Wyeth LLC, Madison, NJ (US)

( * ) Notice: Subject to any disclaimer, the term of this patent is extended or adjusted under 35 U.S.C. 154(b) by 492 days.

(21) Appl. No.: 12/251,924

(22) Filed: Oct. 15, 2008
(Under 37 CFR 1.47)

(65) Prior Publication Data
US 2009/0176827 A1    Jul. 9, 2009

Related U.S. Application Data

(60) Provisional application No. 61/124,796, filed on Oct. 17, 2007.

(51) Int. Cl.
C07D 215/44    (2006.01)

(52) U.S. Cl. .................................................... 546/160
(58) Field of Classification Search .................. 546/160
See application file for complete search history.

(56) References Cited

U.S. PATENT DOCUMENTS

| 6,288,082 | B1 | 9/2001 | Wissner et al. |
| 2005/0059678 | A1 | 3/2005 | Wissner et al. |
| 2006/0270668 | A1* | 11/2006 | Chew et al. ................ 514/232.5 |
| 2006/0270669 | A1 | 11/2006 | Chew et al. |

OTHER PUBLICATIONS

ICH Expert Working Group: "Impurities in New Drug Substances Q3A (R),"International Conference on Harmonisation of Technical Requirements for Registration of Pharmaceuticals for Human Use (Online) 2002, XP002522324; URL: http://www.ikev.org/haber/stabilite/cd/10%201.9%20ICH%20Q3AR%20forCD.pdf.

* cited by examiner

*Primary Examiner* — Nizal Chandrakumar
(74) *Attorney, Agent, or Firm* — David Rubin

(57) ABSTRACT

The present invention relates to maleate salt forms of (E)-N-{4-[3-chloro-4-(2-pyridinylmethoxy)anilino]-3-cyano-7-ethoxy-6-quinolinyl}-4-(dimethylamino)-2-butenamide, methods of preparing crystalline maleate salt forms, the associated compounds, and pharmaceutical compositions containing the same. The maleate salts are useful in treating cancers, particularly those affected by kinases of the epidermal growth factor receptor family.

4 Claims, 8 Drawing Sheets

MALEATE SALTS OF (E)-N-{4-[3-CHLORO-4-(2-PYRIDINYLMETHOXY)ANILINO]-3-CYANO-7-ETHOXY-6-QUINOLINYL}-4-(DIMETHYLAMINO)-2-BUTENAMIDE AND CRYSTALLINE FORMS THEREOF

CROSS-REFERENCE TO RELATED APPLICATIONS

This application claims the benefit under 35 U.S.C. §119 (e) to co-pending U.S. Provisional Application Ser. No. 61/124,796, filed Oct. 17, 2007, which is hereby incorporated by reference in its entirety.

FIELD OF THE INVENTION

This invention is directed to maleate salts of (E)-N-{4-[3-chloro-4-(2-pyridinylmethoxy)anilino]-3-cyano-7-ethoxy-6-quinolinyl}-4-(dimethylamino)-2-butenamide, crystalline forms thereof, methods of preparing the salts, associated compounds, pharmaceutical compositions containing the maleate salt, and methods for their use. Maleate salts of (E)-N-{4-[3-chloro-4-(2-pyridinylmethoxy)anilino]-3-cyano-7-ethoxy-6-quinolinyl}-4-(dimethylamino)-2-butenamide are useful in the treatment of cancer.

BACKGROUND OF THE INVENTION

Compounds derived from 3-cyanoquinoline have been shown to have anti-tumor activity, which may make them useful as chemotherapeutic agents in treating various cancers, including but not limited to, pancreatic cancer, melanoma, lymphatic cancer, parotid tumors, Barrett's esophagus, esophageal carcinomas, head and neck tumors, ovarian cancer, breast cancer, epidermoid tumors, cancers of major organs, such as kidney, bladder, larynx, stomach, and lung, colonic polyps and colorectal cancer and prostate cancer. Examples of compounds derived from 3-cyanoquinoline are disclosed and shown to possess anti-tumor activity in U.S. Pat. Nos. 6,002,008; 6,432,979; and 6,288,082. One limitation of certain 3-cyanoquinoline compounds is that they are not water soluble in a free base form.

The crystalline form of a particular drug as a salt, a hydrate and/or any polymorph thereof is often one important determinant of the drug's ease of preparation, stability, water solubility, storage stability, ease of formulation and in-vivo pharmacology. It is possible that one crystalline form is preferable over another where certain aspects such as ease of preparation, stability, water solubility and/or superior pharmacokinetics are deemed to be critical. Crystalline forms of (E)-N-{4-[3-chloro-4-(2-pyridinylmethoxy)anilino]-3-cyano-7-ethoxy-6-quinolinyl}-4-(dimethylamino)-2-butenamide salts that possess a higher degree of water solubility than the free base but are stable fulfill an unmet need for stable, crystalline, water-soluble forms of substituted 3-cyanoquinoline compounds that selectively inhibit kinase activity, which in turn inhibit cell proliferation and tumorigenesis.

SUMMARY OF THE INVENTION

The present invention provides crystalline forms of (E)-N-{4-[3-chloro-4-(2-pyridinylmethoxy)anilino]-3-cyano-7-ethoxy-6-quinolinyl}-4-(dimethylamino)-2-butenamide maleate, which have been isolated and characterized as: an anhydrous form, a monohydrate form, and a mixture of the anhydrous and the monohydrate forms (referred to as a partial hydrate form). The invention is also directed to methods for using this maleate salt and the crystalline forms thereof, and pharmaceutical formulations containing them.

The invention provides an isolated crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I), characterized by differential scanning calorimetry (DSC), as exhibiting an onset temperature in the range of about 196-204° C., at which melting and decomposition occur.

The invention also provides an isolated crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I), wherein the maleate salt is characterized by X-ray diffraction (XRD) peaks at the following angles (±0.20°) of 2θ in its X-ray diffraction pattern: 6.16, 7.38, 8.75, 10.20, 12.24, 12.61, 14.65, 15.75, 17.33, 18.64, 19.99, 20.66, 21.32, 22.30, 23.18, 24.10, 24.69, 25.49, 26.09, 26.54, 27.52, 28.62, and 29.43. In a separate embodiment, the isolated crystalline form of anhydrous (E)-N-{4-[3-chloro-4-(2-pyridinyl methoxy)anilino]-3-cyano-7-ethoxy-6-quinolinyl}-4-(dimethylamino)-2-butenamide maleate exhibits an X-ray diffraction pattern wherein all of the X-ray diffraction peaks are at about the 2θ angles disclosed above.

The invention provides an isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate (Form II), exhibiting water loss at about 50° C. and characterized by a water content of about 2.5 to 2.7% by weight, based on the weight of the compound as a monohydrate.

The invention also provides an isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate (Form II), wherein the maleate salt is characterized by XRD peaks at the following angles (±0.20°) of 2θ in its X-ray diffraction pattern: 6.53, 8.43, 10.16, 12.19, 12.47, 13.01, 15.17, 16.76, 17.95, 19.86, 21.11, 21.88, 23.22, 23.78, 25.69, 26.17, 27.06, 27.58, 28.26, 28.73, and 29.77. In a separate embodiment, the isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate exhibits an X-ray diffraction pattern wherein all of the X-ray diffraction peaks are at about the 2θ angles disclosed above.

The invention also provides an isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate (Form II), characterized by DSC, as exhibiting an onset temperature in the range of 196-204° C., at which melting and decomposition occur, especially at a transition temperature of about 203.8° C.

The invention provides an isolated crystalline form of a partially hydrated (E)-N-{4-[3-chloro-4-(2-pyridinylmethoxy)anilino]-3-cyano-7-ethoxy-6-quinolinyl}-4-(dimethylamino)-2-butenamide maleate (Form II), characterized by a water content of about 0.8 to about 2.4% by weight, including about 1.5% to about 2.3% by weight, based on the weight of the compound.

The present invention provides a method of preparing the maleate salt by mixing (E)-N-{4-[3-chloro-4-(2-pyridinylmethoxy)anilino]-3-cyano-7-ethoxy-6-quinolinyl}-4-(dimethylamino)-2-butenamide (the free base) with maleic acid and dissolving the mixture in a water-alcohol solution at an elevated temperature. The resulting solution is cooled and the cooled solution contains (E)-N-{4-[3-chloro-4-(2-pyridinylmethoxy)anilino]-3-cyano-7-ethoxy-6-quinolinyl}-4-(dimethylamino)-2-butenamide maleate.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate (Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent and an amount of water and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate (Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent; adding a solution comprising an amount of water in an organic solvent; and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate(Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent and an amount of water and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate(Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent comprising an amount of water and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate(Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent comprising an amount of water over a period of days and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in anhydrous form (Form I) comprising the step of: drying under vacuum (E)-N-{4-[3-chloro-4-(2-pyridinylmethoxy)anilino]-3-cyano-7-ethoxy-6-quinolinyl}-4-(dimethylamino)-2-butenamide maleate as a monohydrate (Form II) at a temperature greater than 30° C. for about 12 to about 48 hours.

The invention also provides a pharmaceutical formulation comprising: (E)-N-{4-[3-chloro-4-(2-pyridinylmethoxy)anilino]-3-cyano-7-ethoxy-6-quinolinyl}-4-(dimethylamino)-2-butenamide maleate and one or more associated compounds having the following structures:

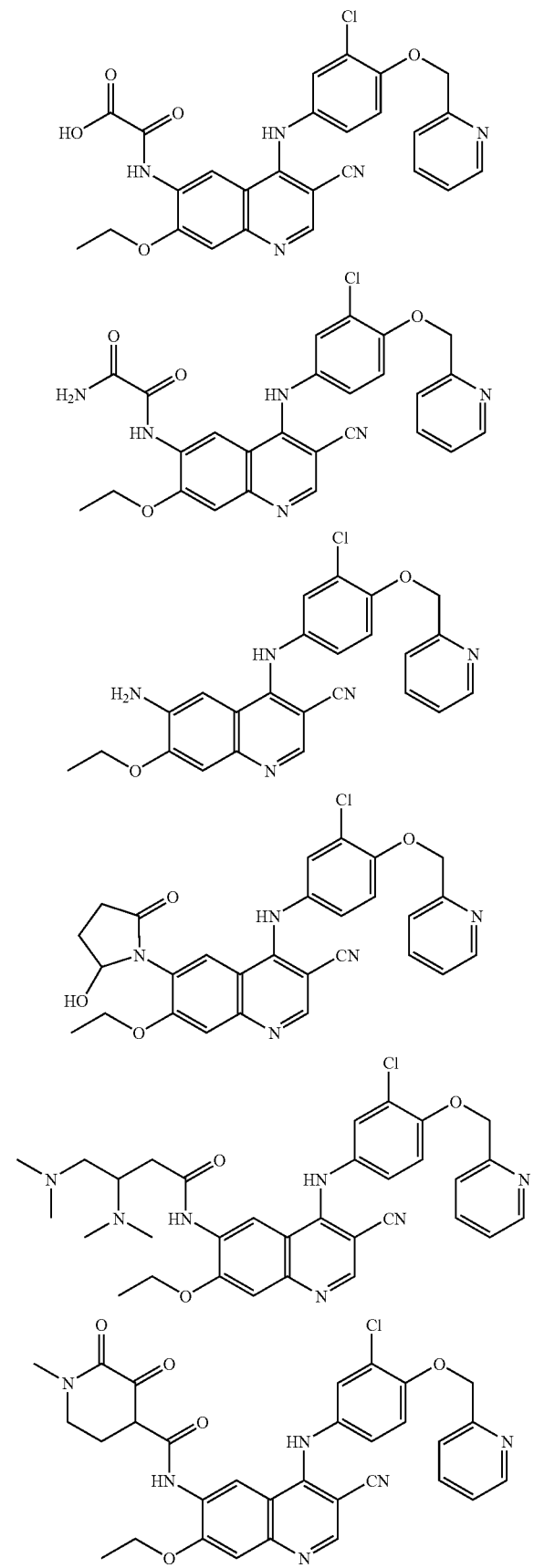

-continued

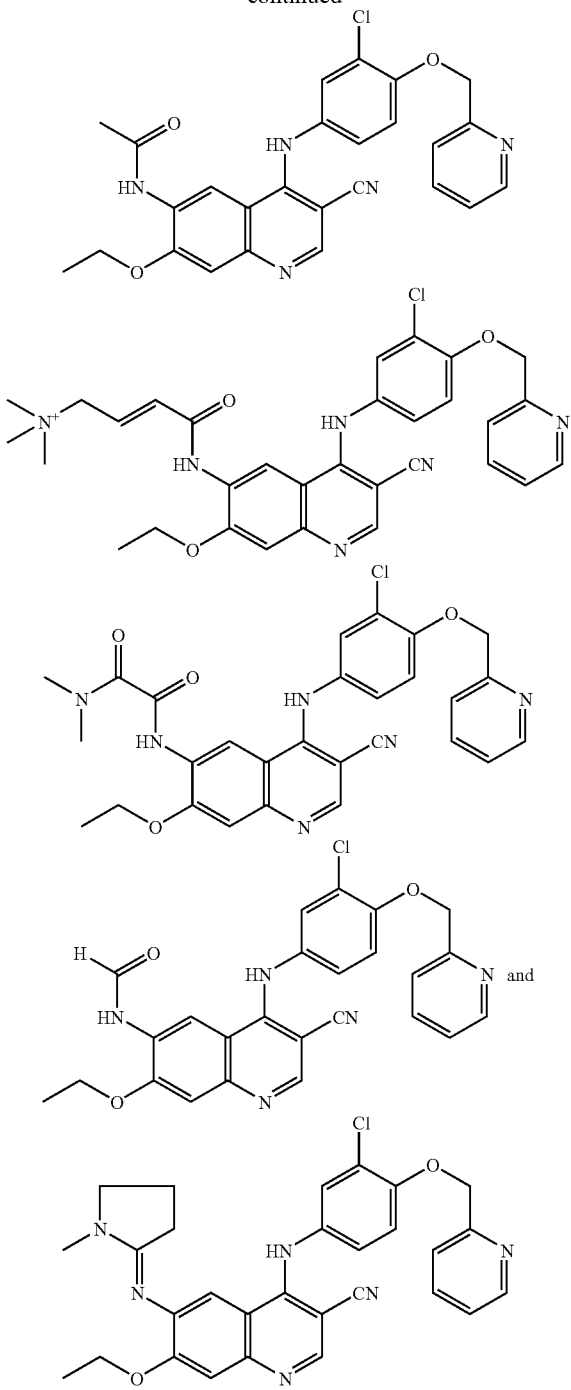

The present invention also provides a pharmaceutical composition for the inhibition of HER-2 kinase activity comprising a therapeutically-effective amount of (E)-N-{4-[3-chloro-4-(2-pyridinylmethoxy)anilino]-3-cyano-7-ethoxy-6-quinolinyl}-4-(dimethylamino)-2-butenamide maleate and a pharmaceutically acceptable carrier. The pharmaceutical composition may also contain one or more of the associated compounds discussed above. The maleate salt may be in an anhydrous form, a monohydrate form, and combinations of these forms.

The present invention also provides a method for preventing, treating, or inhibiting cancer by administering a therapeutically-effective amount of (E)-N-{4-[3-chloro-4-(2-pyridinylmethoxy)anilino]-3-cyano-7-ethoxy-6-quinolinyl}-4-(dimethylamino)-2-butenamide maleate to a subject. The subject may be a mammal, and more specifically, a human. The maleate salt may be administered in its anhydrous form, monohydrate form, or partially hydrated form. One or more of the associated compounds discussed above may also be administered during this method.

Figure 1:
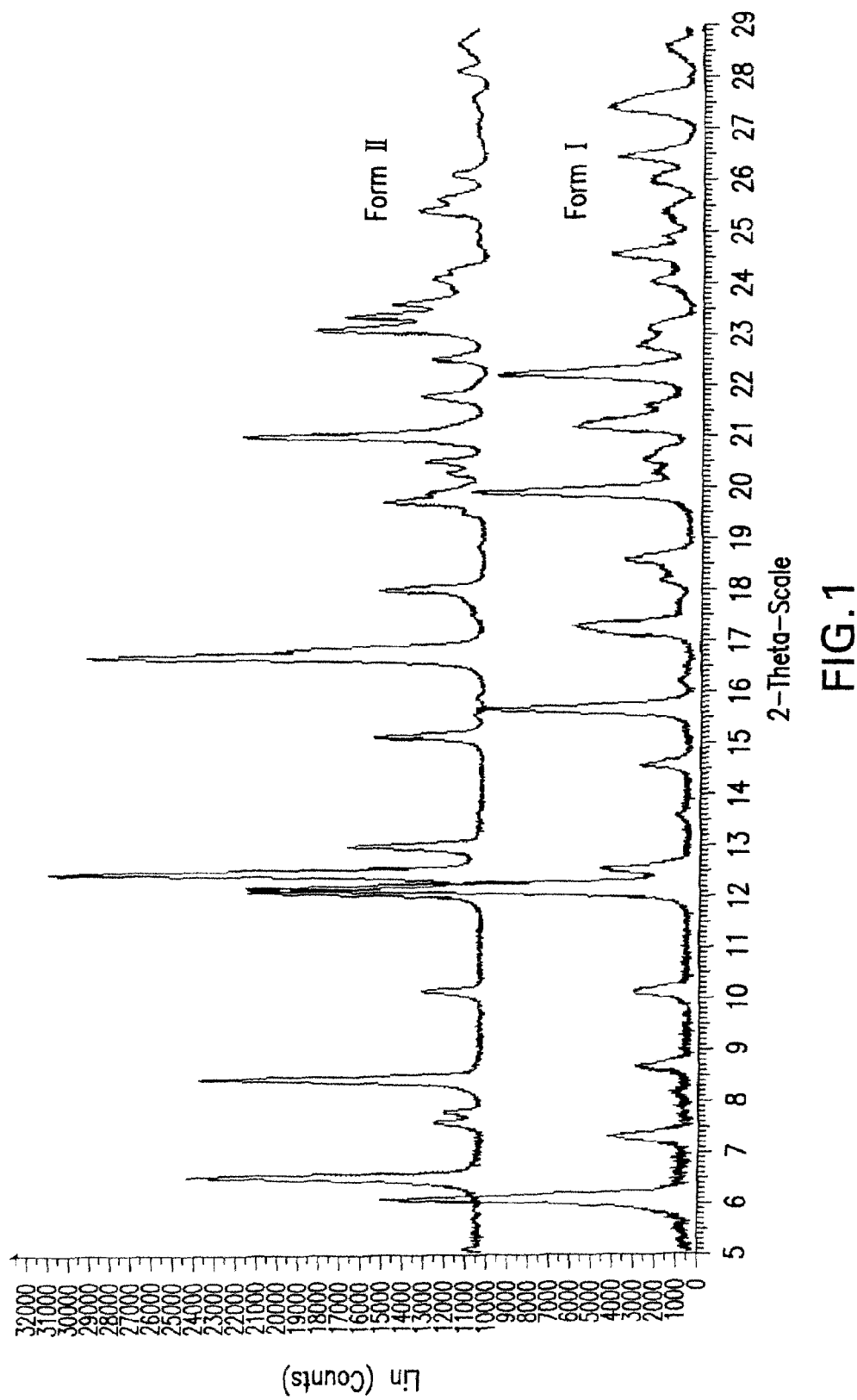
FIG. 1. The XRD scans of two crystalline forms of (E)-N-{4-[3-chloro-4-(2-pyridinylmethoxy)anilino]-3-cyano-7-ethoxy-6-quinolinyl}-4-(dimethylamino)-2-butenamide maleate, anhydrous Form I and monohydrate Form II.

DETAILED DESCRIPTION OF THE INVENTION (E)-N-{4-[3-chloro-4-(2-pyridinylmethoxy)anilino]-3-cyano-7-ethoxy-6-quinolinyl}-4-(dimethylamino)-2-butenamide is an irreversible inhibitor to Her-2 (also known as ErbB-2 or neu) kinase, a member of the epidermal growth factor receptor (EGFR) family. EGFR family members have been implicated in tumorigenesis and associated with poor prognosis in tumor types in humans. The structure of the (E)-N-{4-[3-chloro-4-(2-pyridinylmethoxy)anilino]-3-cyano-7-ethoxy-6-quinolinyl}-4-(dimethylamino)-2-butenamide in the form of a free base is shown below:

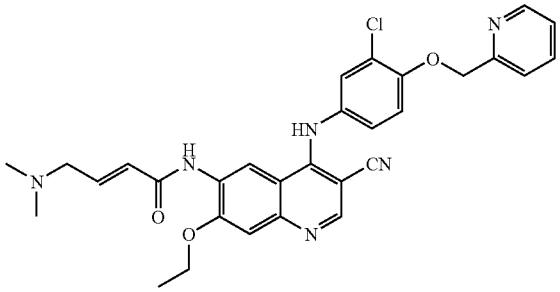

The compound (E)-N-{4-[3-chloro-4-(2-pyridinyl methoxy)anilino]-3-cyano-7-ethoxy-6-quinolinyl}-4-(dimethylamino)-2-butenamide in the form of a free base is described in U.S. Pat. No. 6,288,082. The compound is classified, based on the Biopharmaceutical Classification System, as a BCS Class IV compound (low water solubility and low permeability). The free base has low solubility in water, with a water solubility of about 1 µg/mL at about pH 7. The water solubility increases with decreasing pH as the compound becomes ionized. This compound is water soluble at gastrointestinal pH, and dissolution is not rate limiting. There is a need for a form of this compound with improved physicochemical properties.

The present invention provides a water-soluble acid addition salt form of (E)-N-{4-[3-chloro-4-(2-pyridinylmethoxy)anilino]-3-cyano-7-ethoxy-6-quinolinyl}-4-(dimethylamino)-2-butenamide. The free base compound is capable of forming salts with a variety of pharmaceutically suitable acids. Pharmaceutically suitable acids include, but are not limited to for example, acetic, fumuric, maleic, methanesulfonic, succinic, sulfuric, tartaric, and p-toluenesulfonic acid. The physicochemical properties of each acid addition salt form were evaluated to screen for an optimal pharmaceutical salt form, as shown in Table 1.

The (E)-N-{4-[3-chloro-4-(2-pyridinylmethoxy)anilino]-3-cyano-7-ethoxy-6-quinolinyl}-4-(dimethylamino)-2-butenamide maleate salt is crystalline and has higher solubility in water as compared to the free base as shown in Table 2.

TABLE 2

SOLUBILITY COMPARISON OF FREE BASE AND MALEATE SALT

| Solvent | free base | Maleate salt |
|---|---|---|
| Water | <LOD* (pH 8.2) | 0.43 mg/mL (pH 5.00) |
| 2% Tween™ 80** in water | 0.05 mg/mL (pH 6.4) | 1.12 mg/mL (pH 5.06) |

*LOD = limit of detection
**Also known as Polysorbate™ 80, a non-ionic solvent prepared from polyoxylated sorbitol and oleic acid.

A comparison of the systemic exposure (SE) data for (E)-N-{4-[3-chloro-4-(2-pyridinylmethoxy)anilino]-3-cyano-7-ethoxy-6-quinolinyl}-4-(dimethylamino)-2-butenamide has been conducted on data extracted from multiple preclinical

TABLE 1

PHYSICOCHEMICAL PROPERTIES OF SALT FORMS OF (E)-N-{4-[3-CHLORO-4-(2-PYRIDINYLMETHOXY)ANILINO]-3-CYANO-7-ETHOXY-6-QUINOLINYL}-4-(DIMETHYLAMINO)-2-BUTENAMIDE

| Salt | Acid/Base Ratio (by NMR) | Crystallinity (by XRD) | Crystallinity (by Microscopy) | DSC* ($T_{apex}$) | TGA (30-150° C.) | Residual Solvents (%) | pH | Solubility (mg/g) |
|---|---|---|---|---|---|---|---|---|
| 1 | Acetate (not a salt) | Crystalline | Crystalline Fine needles | 116° C., 186° C. | 6.46% | 6.9 | 8.34 | <LOD |
| 2 | Mesylate (1:1) | Crystalline (moderate) | Crystalline Fine needles | 88° C., 141° C. | 5.03% | 0.56 | 4.29 | 10.62 |
| 3 | Tosylate (1:1) | Crystalline (low) | Crystalline Irregular particles | 159° C. | 2.1% | 1.17 | 4.72 | 6.89 |
| 4 | Maleate (1:1) | Crystalline | Crystalline Irregular particles | 195° C. | 0.5% | 1.19 | 5.11 | 0.37 |
| 5 | Fumarate (1:1) | Amorphous | Amorphous | Unclear | 2.71% | 0.13 | 3.53 | 0.78 |
| 6 | Tartrate (1:1) | Amorphous | Amorphous | Unclear | 2.98% | 0.14 | 3.49 | 0.66 |
| 7 | Succinate (1:1) | Amorphous w/crystalline features | Amorphous w/crystalline features | 109° C. | 1.73% | 0.86 | 3.97 | 3.08 |
| 8 | Citrate (1:1) | Amorphous | Amorphous | Unclear | 2.86% | 0.56 | 3.45 | 0.30 |
| 9 | Sulfate (2:1 assumed) | Amorphous | Amorphous | 149° C. | 4.42% | 0.0 | 3.01 | 1.07 |

* Minor endotherms and some broad endotherms are not listed.

Of the nine salts, the maleate salt exhibited advantageous physicochemical properties. The maleate salt was crystalline and less hygroscopic. The mesylate salt was hygroscopic and less crystalline. The tosylate salt was even less attractive, primarily due to its higher molecular weight and safety concerns. Although the acetate "salt" appeared to be crystalline, NMR revealed that the product prepared from acetic acid was in fact not a salt. The fact that the product prepared from acetic acid was insoluble in water with a resulting alkaline pH confirmed that it largely retained the free base properties.

studies in the rat. The analysis of these data indicated that, in the rat, administration of the compound as the maleate salt provided a two-fold increase in AUC (area under concentration), as compared to the free base, when administered at a dose range of 5 to 45 mg/kg. The systemic availability of the compound as the free base was relatively low (20%), and the presence of significant amounts of drug in the feces could be attributed to poor absorption. The increased solubility of the maleate salt appears to enhance the absorption of the compound in the rat. Table 3 presents the plasma compound mean AUC and $C_{max}$ data observed in rats.

TABLE 3

MEAN (SE) COMPOUND PHARMACOKINETICS IN RATS

| Form | Dose (mg/kg) | Day | N | $C_{max}$ (ng/mL) Male | $C_{max}$ (ng/mL) Female | $AUC_{0-24}$ (ng·hr/mL) Male | $AUC_{0-24}$ (ng·hr/mL) Female | AUC/Dose Male | AUC/Dose Female |
|---|---|---|---|---|---|---|---|---|---|
| Maleate Salt | 5 | 28 | 3 | 1199 (138) | 1381 (220) | 8224 (630) | 9534 (844) | 1645 (126) | 1907 (169) |
| Free Base | 10 | 10 | 3 | 814 (116) | ND | 6785 (642) | ND | 678 (64) | ND |
| Maleate Salt | 15 | 28 | 3 | 3418 (802) | 3555 (628) | 30217 (2666) | 34177 (2654) | 2014 (178) | 2278 (177) |
| Free Base | 20 | 1 | 4 | 1009 (194) | ND | 8513[a] (1616) | ND | 426 (81) | ND |
| Free Base | 30 | 10 | 3 | 1654 (65) | 2437 (708) | 20389 (2331) | 24956 (4318) | 680 (78) | 832 (145) |
| Maleate Salt | 45 | 28 | 3 | 4615 (560) | 4562 (406) | 65062 (4791) | 75640 (6352) | 1446 (106) | 1681 (141) |
| Free Base | 100 | 10 | 3 | 3818 (656) | ND | 58270 (12513) | ND | 583 (125) | ND |

[a]$AUC_{0-\infty}$
ND = Not Dosed
Maleate salt administered at 10 mL/kg with suspensions of 0.5 to 4.5 mg/mL
Free base administered at 10 mL/kg with suspensions of 1 to 10 mg/mL The maleate salt consistently and reproducibly exhibited beneficial physicochemical properties, as shown in Table 4.

TABLE 4

PHYSICOCHEMICAL PROPERTIES OF MALEATE SALT PILOT BATCHES

| Run | Batch Size | Crystallinity (Microscopy) | Particle Size* | DSC (Tonset °C.) | % Moisture (KF) | Residual Solvent (%) | Solution pH | Aqueous Solubility*** (mg/g) | HPLC Purity (%) |
|---|---|---|---|---|---|---|---|---|---|
| 1 | 0.5 g | Crystalline Fine rods | 5-10 μm | 195 | 0.59 | 1.19 | 5.11 | 0.37 | 99.38 |
| 2 | 6.6 g | Crystalline Fine needles | 5-50 μm | 197.6 | 0.36 | 0.1 EtOAc | 5.10 | 0.50 | 99.70 |
| 3 | 4 g | Crystalline Fine needles | 25-100 μm | 196.3 | 0.35 | ND** | 5.15 | 0.44 | 99.52 |

*Particle size is estimated from the captured image from light microscope.
**ND: not determined
***s the free base In addition to exhibiting poor water solubility, the compound (E)-N-{4-[3-chloro-4-(2-pyridinylmethoxy)anilino]-3-cyano-7-ethoxy-6-quinolinyl}-4-(dimethylamino)-2-butenamide in the form of a free base interacts with emectic receptors in the stomach, giving rise to diarrhea in mammals. The maleate salt of (E)-N-{4-[3-chloro-4-(2-pyridinylmethoxy)anilino]-3-cyano-7-ethoxy-6-quinolinyl}-4-(dimethylamino)-2-butenamide, however, unexpectedly mitigates such problems and minimizes emectic receptor interactions in mammals.

The maleate salt is prepared by mixing (E)-N-{4-[3-chloro-4-(2-pyridinylmethoxy)anilino]-3-cyano-7-ethoxy-6-quinolinyl}-4-(dimethylamino)-2-butenamide (the free base) with maleic acid and dissolving the mixture in a water-alcohol solution at an elevated temperature. The resulting solution is cooled and the cooled solution contains (E)-N-{4-[3-chloro-4-(2-pyridinylmethoxy)anilino]-3-cyano-7-ethoxy-6-quinolinyl}-4-(dimethylamino)-2-butenamide maleate. According to one embodiment, (E)-N-{4-[3-chloro-4-(2-pyridinylmethoxy)anilino]-3-cyano-7-ethoxy-6-quinolinyl}-4-(dimethylamino)-2-butenamide maleate is prepared by combining maleic acid and the free base in a solution of water and n-propanol, as described in Scheme 1.

SCHEME 1

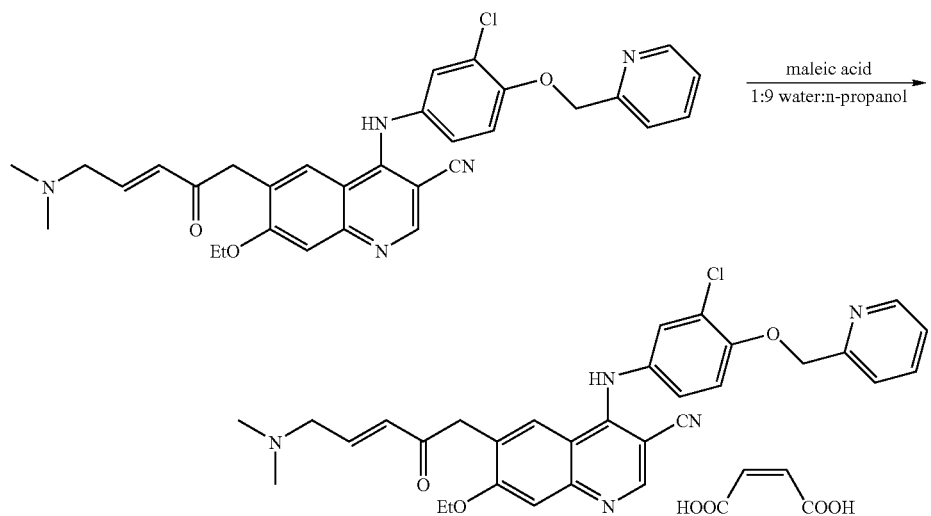

The reaction of the free base and maleic acid occurs at an elevated temperature of from about 40° C. to about 60° C., preferably between about 40° C. to about 50° C. The ratio of water:n-propanol may vary, for example between about 1:10 to about 1:5, and the optimal ratio of water:n-propanol is about 1:9. The water-alcohol solution may comprise from about 5% to about 20% by volume water and from about 80% to about 95% by volume alcohol. The alcohol may be n-propanol. In one embodiment, the water-alcohol solution comprises about 10% by volume water and about 90% by volume n-propanol. The volume of the solvent solution may be between about 8 to about 25 volumes, including about 10 to about 12 volumes. About 1.0-1.2 equivalents of maleic acid is used per equivalent of the free base, preferably about 1.03 equivalents of maleic acid per equivalent of the free base.

The resulting solution of the maleate salt may be clarified by filtration prior to cooling. The cooling step may be continued until the solution reaches a temperature of about 45° C. or less, including a temperature of about 39° C. or less, and more preferably to about 30° C. or less. In one embodiment, the solution is filtered after cooling to about room temperature, preferably from about 23° C. to about 25° C. Typically, the maleate salt begins to crystallize out of solution once the temperature reaches 37° C. or below. The solution may be allowed to sit for at least 12 hours, preferably about 12 to about 15 hours at room temperature, and is then filtered and washed to recover the crystalline maleate salt product. The resulting filter cake may be washed with the same or a different water-alcohol solution to obtain the product. The product may be dried to obtain crystalline (E)-N-{4-[3-chloro-4-(2-pyridinylmethoxy)anilino]-3-cyano-7-ethoxy-6-quinolinyl}-4-(dimethylamino)-2-butenamide maleate. At this point, the maleate salt product recovered and isolated is typically in the form of the monohydrate form of the maleate salt.

The product may be dried under vacuum with heating to make the anhydrous form of the maleate salt (Form I) at about 70 to about 95% yield, preferably about 80 to about 95% yield. This product is usually better than about 98% pure, and often about 99% pure. Typically, the drying process is performed over about 12 to about 48 hours to get complete conversion of the anhydrous form of the maleate salt to the monohydrate form of the maleate salt (Form II). Shorter drying times generally result in mixtures of the two crystalline forms. The drying process is often performed at temperatures greater than room temperature. In one embodiment, drying of the maleate salt is performed at a temperature greater than about 30° C., preferably from about 40° C. to about 60° C., and in another embodiment at about 50° C.

The maleate salt is soluble in many polar solvents, which will be known to one skilled in the art, but dimethyl sulfoxide (DMSO) is often used if a small solvent volume is desired. The DMSO solution can be heated to about 45° C. to about 60° C. to further enhance solubility. Once the anhydrous maleate salt is in solution, water may be added, typically quickly, causing the crystallization that provides the crystalline monohydrate form upon filtration. The anhydrous salt may be dissolved in a solvent, for example DMSO, and to this solution may be added an aqueous solution of water and an organic solvent, for example such as tetrahydrofuran (THF), isopropanol (IPA), n-propanol, acetone, ethanol, methanol, and acetonitrile. In one embodiment, the organic solvent used is IPA, in another embodiment it is n-propanol, and in a third embodiment a mixture of these two organic solvents is used. The water content of the aqueous solution can be as little as 5%, but may be about 7.5% or greater, and in one embodiment is between about 10% and about 15%. The resulting solution then may be allowed to sit for up to about 24 hours, and in one embodiment is allowed to sit for between about 12 hours and about 24 hours, to allow for crystallization to occur. Filtration of the mixture yields a crystalline monohydrate form of the maleate salt. For purposes of this invention, the term "organic solvent and water" refers to a solution of an organic solvent, such as for example tetrahydrofuran (THF), DMSO, methanol, ethanol, isopropyl alcohol or acetonitrile, and water wherein the organic solvent comprises greater then 50% of the solution by volume.

The invented maleate salt of (E)-N-{4-[3-chloro-4-(2-pyridinylmethoxy)anilino]-3-cyano-7-ethoxy-6-quinolinyl}-4-(dimethylamino)-2-butenamide was isolated in three different crystalline forms: an anhydrous form (Form I), a monohydrate form (Form II) and a partially hydrated form (Form III), which comprises a mixture of Form I and Form II. According to one embodiment, the anhydrous form of (E)-N-{4-[3-chloro-4-(2-pyridinylmethoxy)anilino]-3-cyano-7-ethoxy-6-quinolinyl}-4-(dimethylamino)-2-butenamide maleate (Form I) is obtained as a crystalline solid by drying the reaction product of (E)-N-{4-[3-chloro-4-(2-pyridinyl-methoxy)anilino]-3-cyano-7-ethoxy-6-quinolinyl}-4-(dimethylamino)-2-butenamide and maleic acid. Drying includes air drying, heating and drying under reduced pressure. In an alternative embodiment, the anhydrous form of (E)-N-{4-[3-chloro-4-(2-pyridinylmethoxy)anilino]-3-cyano-7-ethoxy-6-quinolinyl}-4-(dimethylamino)-2-butenamide maleate (Form I) is obtained as a crystalline solid by drying the monohydrate form of (E)-N-{4-[3-chloro-4-(2-pyridinylmethoxy)anilino]-3-cyano-7-ethoxy-6-quinolinyl}-4-(dimethylamino)-2-butenamide maleate (Form II).

The isolated crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I), is characterized by differential scanning calorimetry (DSC), as exhibiting an onset temperature in the range of about 196-204° C., at which melting and decomposition occur.

The anhydrous maleate salt (Form I) is characterized by X-ray diffraction (XRD) peaks at the following angles (±0.20°) of 2θ in its X-ray diffraction pattern: 6.16, 7.38, 8.75, 10.20, 12.24, 12.61, 14.65, 15.75, 17.33, 18.64, 19.99, 20.66, 21.32, 22.30, 23.18, 24.10, 24.69, 25.49, 26.09, 26.54, 27.52, 28.62, and 29.43. In a separate embodiment, the isolated crystalline form of an hydrous (E)-N-{4-[3-chloro-4-(2-pyridinyl methoxy)anilino]-3-cyano-7-ethoxy-6-quinolinyl}-4-(dimethylamino)-2-butenamide maleate (Form I) exhibits an X-ray diffraction pattern wherein all of the X-ray diffraction peaks are at about the 2θ angles disclosed above.

According to one embodiment, (E)-N-{4-[3-chloro-4-(2-pyridinylmethoxy)anilino]-3-cyano-7-ethoxy-6-quinolinyl}-4-(dimethylamino)-2-butenamide maleate is prepared in the form of a crystalline monohydrate (Form II) by mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent and an amount of water and filtering crystalline monohydrate that precipitates from the mixture.

In a separate embodiment, (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate (Form II) is prepared by mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent; adding a solution comprising an amount of water in an organic solvent; and filtering crystalline monohydrate that precipitates from the mixture.

In another embodiment, (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate (Form II) is prepared by mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent comprising an amount of water over a period of days and filtering crystalline monohydrate that precipitates from the mixture. The period of days is suitably about 1-20 days. The isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate (Form II), exhibits water loss at about 50° C., as measured by DSC, and is characterized by a water content of about 2.5 to 2.7% by weight, as measured by thermal gravimetric analysis (TGA), based on the weight of the compound as a monohydrate. The water content of the monohydrate form of the maleate salt was also measured by Karl Fischer titration.

(E)-N-{4-[3-chloro-4-(2-pyridinylmethoxy)anilino]-3-cyano-7-ethoxy-6-quinolinyl}-4-(dimethylamino)-2-butenamide maleate as a monohydrate (Form II) is characterized by X-ray diffraction peaks (XRD) at the following angles (±0.20°) of 2θ in its X-ray diffraction pattern: 6.53, 8.43, 10.16, 12.19, 12.47, 13.01, 15.17, 16.76, 17.95, 19.86, 21.11, 21.88, 23.22, 23.78, 25.69, 26.17, 27.06, 27.58, 28.26, 28.73, and 29.77. In a separate embodiment, the isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate exhibits an X-ray diffraction pattern wherein all of the X-ray diffraction peaks are at about the 2θ angles disclosed above.

As used herein, the term isolated means that more than 50% of the crystalline (E)-N-{4-[3-chloro-4-(2-pyridinylmethoxy)anilino]-3-cyano-7-ethoxy-6-quinolinyl}-4-(dimethylamino)-2-butenamide maleate salt present is one of Forms I and II. In one embodiment, at least 70% of the crystal line (E)-N-{4-[3-chloro-4-(2-pyridinylmethoxy)anilino]-3-cyano-7-ethoxy-6-quinolinyl}-4-(dimethylamino)-2-butenamide maleate salt present is one of Forms I and II. In a second embodiment, at least 80% of the maleate salt present is one of Forms I and II. In a third embodiment, at least 90% of the maleate salt present is one of Forms I and II.

The two crystalline forms of (E)-N-{4-[3-chloro-4-(2-pyridinylmethoxy)anilino]-3-cyano-7-ethoxy-6-quinolinyl}-4-(dimethylamino)-2-butenamide maleate, exhibit distinct XRD patterns and peaks. The XRD pattern for each maleate salt form is unique to that salt form. The XRD patterns of Forms I and II were determined by using techniques and equipment known to those skilled in the art of analytical chemistry and X-ray crystallography. XRD patterns were produced using powder samples and are comprised of a set of diffraction peaks, which can be expressed in 2 theta angles, d-spacing and/or relative peak intensities. The XRD patterns are shown in FIGS. 1, 5, 6, 7, and 8. Collection parameters for the X-ray data provided in FIGS. 1, 7 and 8 were as follows: voltage 40 kV; current 40.0 mA; 5.00-30.00 degree scan range; Bruker D8 Advance instrument; scan step size 0.01°; total scan time 30 minutes; using a Vantec-1 detector and Ni filter. The X-ray data in FIGS. 5 and 6 were collected as follows: voltage 30 kV; current 15 mA; 3-40 degree scan range; 2.00°/min; Rigaku Miniflex bench top X-ray diffractometer.

The two-theta diffraction angles and the corresponding d-spacing values account for the positions of the peaks found in a XRD pattern. D-spacing values are calculated with observed two theta angles and copper Kα1 wavelength using the Bragg equation. Variations in these numbers can result from using different diffractometers and also from the method of sample preparation. However, more variation can be expected for the relative peak intensities. Therefore, identification of the various forms should be based upon the observed two-theta angles and the d-spacings, and less importance should be given to the intensities. One skilled in the art would understand that the XRD patterns of Forms I and II obtained as described herein could contain additional peaks. Additionally, a skilled artisan would recognize that whether all the peaks are observed for a given form may be highly dependent on the concentration level of the form. FIG. 1 illustrates XRD scans of the two crystalline forms of the maleate salt, Form I and II. The crystalline anhydrous maleate salt form, Form I, is shown on the bottom, while the crystalline monohydrate form of the maleate salt, Form II, is shown on top.

Figure 2:
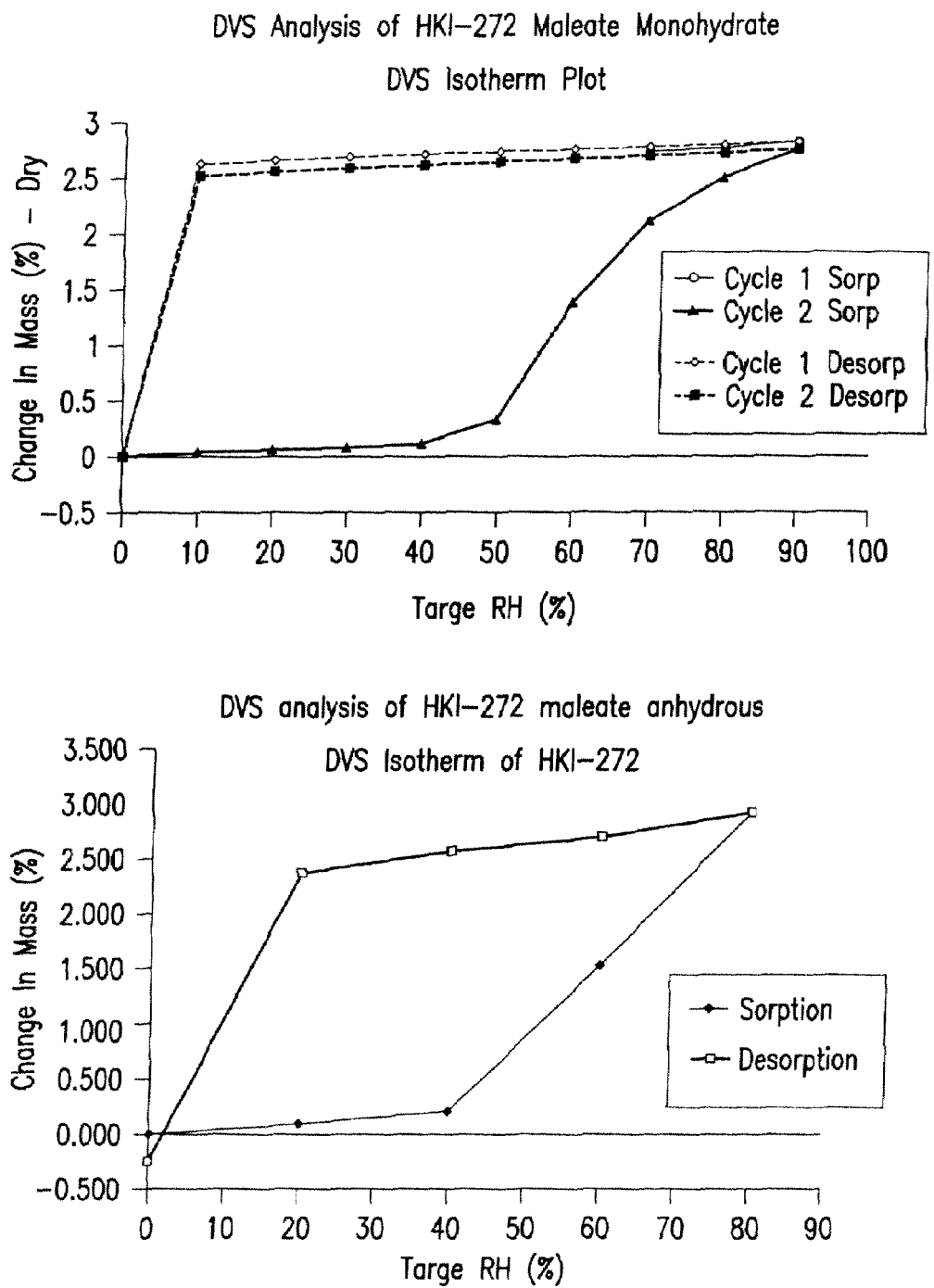
FIG. 2. A dynamic vapor sorption (DSV) isotherm plot of (E)-N-{4-[3-chloro-4-(2-pyridinylmethoxy)anilino]-3-cyano-7-ethoxy-6-quinolinyl}-4-(dimethylamino)-2-butenamide maleate, Forms I and II.

The relative stability and hygroscopicity of the two crystalline forms of the maleate salt was studied in detail by dynamic vapor sorption (DVS). The anhydrous form of the maleate salt absorbs water easily and converts to the crystalline monohydrate form of the maleate salt. Upon drying or a drop in the relative humidity, the crystalline monohydrate form of the maleate salt converts to the anhydrous form of the maleate salt, as summarized in FIG. 2. FIG. 2 is a dynamic vapor sorption isotherm plot which shows that (E)-N-{4-[3-chloro-4-(2-pyridinylmethoxy)anilino]-3-cyano-7-ethoxy-6-quinolinyl}-4-(dimethylamino)-2-butenamide maleate, Form I, gains moisture above 40% relative humidity (RH), especially at 60% RH and above. FIG. 2 also shows that Form II loses water at 20% RH and below, especially at 10% RH and below. DVS was performed under the following conditions: RH was set at 0%, 30%, 52.5%, 75% and 90%, with the sample exposed for 3 hours at each RH for two full cycles.

Figure 3:
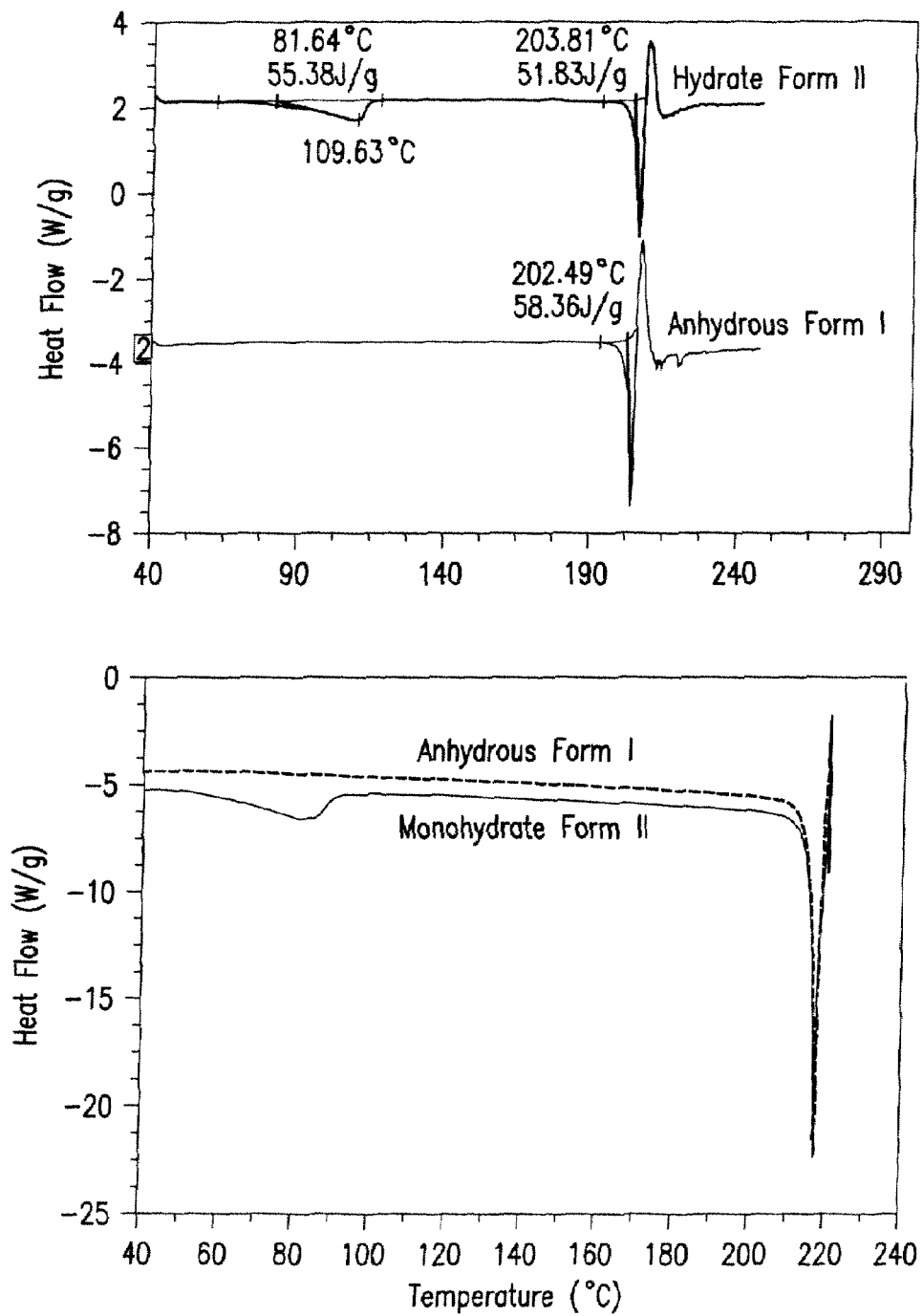
FIG. 3. A differential scanning calorimeter (DSC) plot of Forms I and II.

The two crystalline forms of (E)-N-{4-[3-chloro-4-(2-pyridinylmethoxy)anilino]-3-cyano-7-ethoxy-6-quinolinyl}-4-(dimethylamino)-2-butenamide maleate exhibit distinct DSC traces. A DSC plot of both Form I and Form II of the maleate salt is summarized in FIG. 3. Form I of the maleate salt exhibits one endothermic peak, indicating a transition temperature of 202.49° C. Form II of the maleate salt exhibits two endothermic peaks, a broad endotherm having an onset temperature of 55° C. corresponding to loss of water and a second endotherm indicating a transition temperature of 202.81° C. The transition temperatures are observed in the range of about 196-204° C. at which melting and decomposition occurs. DSC data, transition temperatures and heat flow, were collected using a TA instrument model Q1000 with the following parameters: 50 mL/min purge gas ($N_2$); scan range 40 to 240° C., scan rate 10° C./min. Pure, crystalline solids have a characteristic transition temperature, the temperature at which point the substance changes state, in the present case the solid transitions to a liquid. The transition between the solid and the liquid is so sharp for small samples of a pure substance that transition temperatures can be measured to 0.1° C. Because it is difficult to heat solids to temperatures above their transition temperatures, and because pure solids tend to transition over a very small temperature range, transition temperatures are often used to help identify compounds. Measurements of the transition temperature of a solid can also provide information about the purity of the substance. Pure, crystalline solids transition over a very narrow range of temperatures, whereas mixtures transition over a broad temperature range. Mixtures also tend to transition at temperatures below the transition temperatures of the pure solids.

Figure 4:
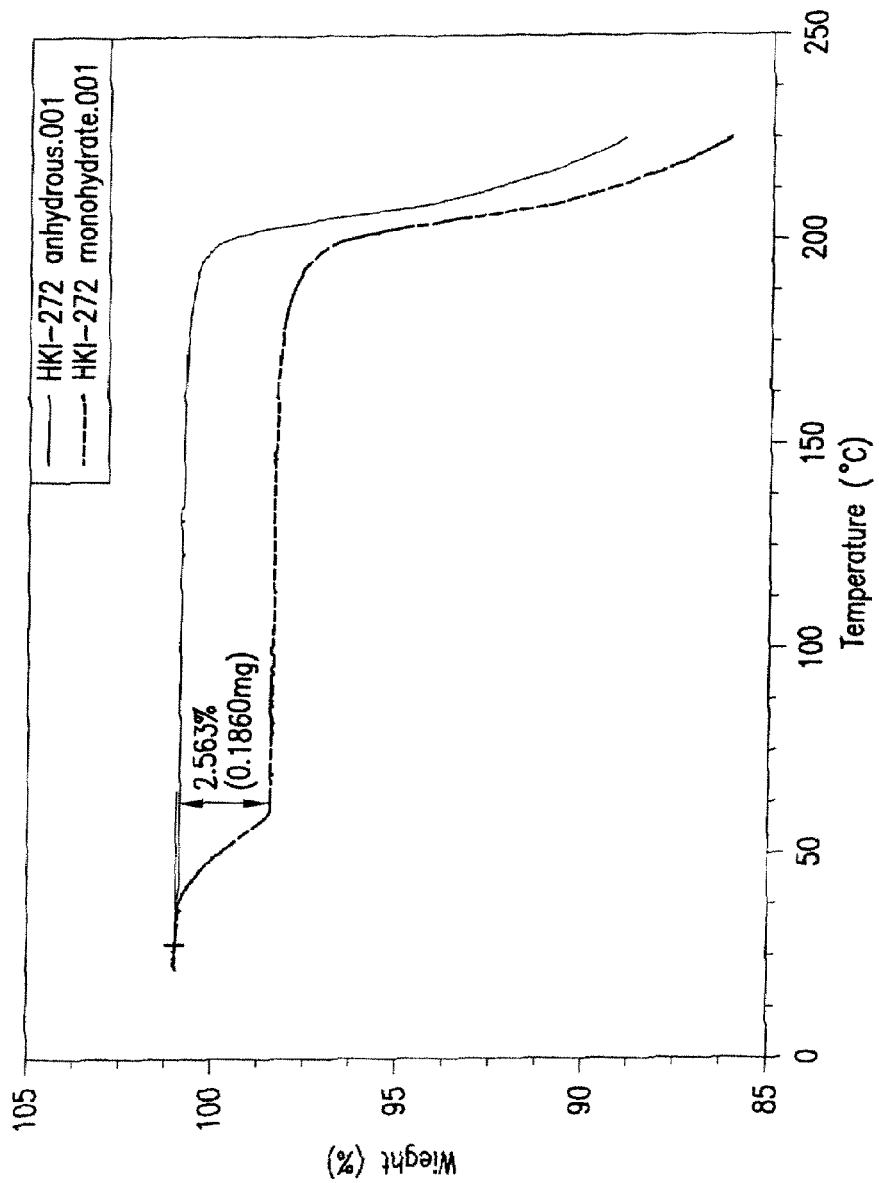
FIG. 4. A theromogravimetric analysis (TGA) plot of Forms I and II.

TGA data of the monohydrate and anhydrous forms of the maleate salt are summarized in FIG. 4. Form II of the maleate salt is characterized by a water content of about 2.5 to 2.7% by weight, as measured by TGA, based on the weight of the compound as a monohydrate. TGA data were collected using a TA Instrument Model Q. A heating rate of 10° C./min between 30-220° C. was used and the TGA chamber was under 40 mL/min flow of nitrogen.

A third crystalline form of the maleate is salt is observed and referred to as the partial hydrate (Form III), as observed from XRD. The partial hydrate is a mixture of Form I and Form II of the maleate salt. The partially hydrated (E)-N-{4-[3-chloro-4-(2-pyridinylmethoxy)anilino]-3-cyano-7-ethoxy-6-quinolinyl}-4-(dimethylamino)-2-butenamide maleate (Form III), is characterized by a water content of about 0.8 to about 2.4% by weight, including about 1.5% to about 2.3% by weight, based on the weight of the compound.

Figure 5:
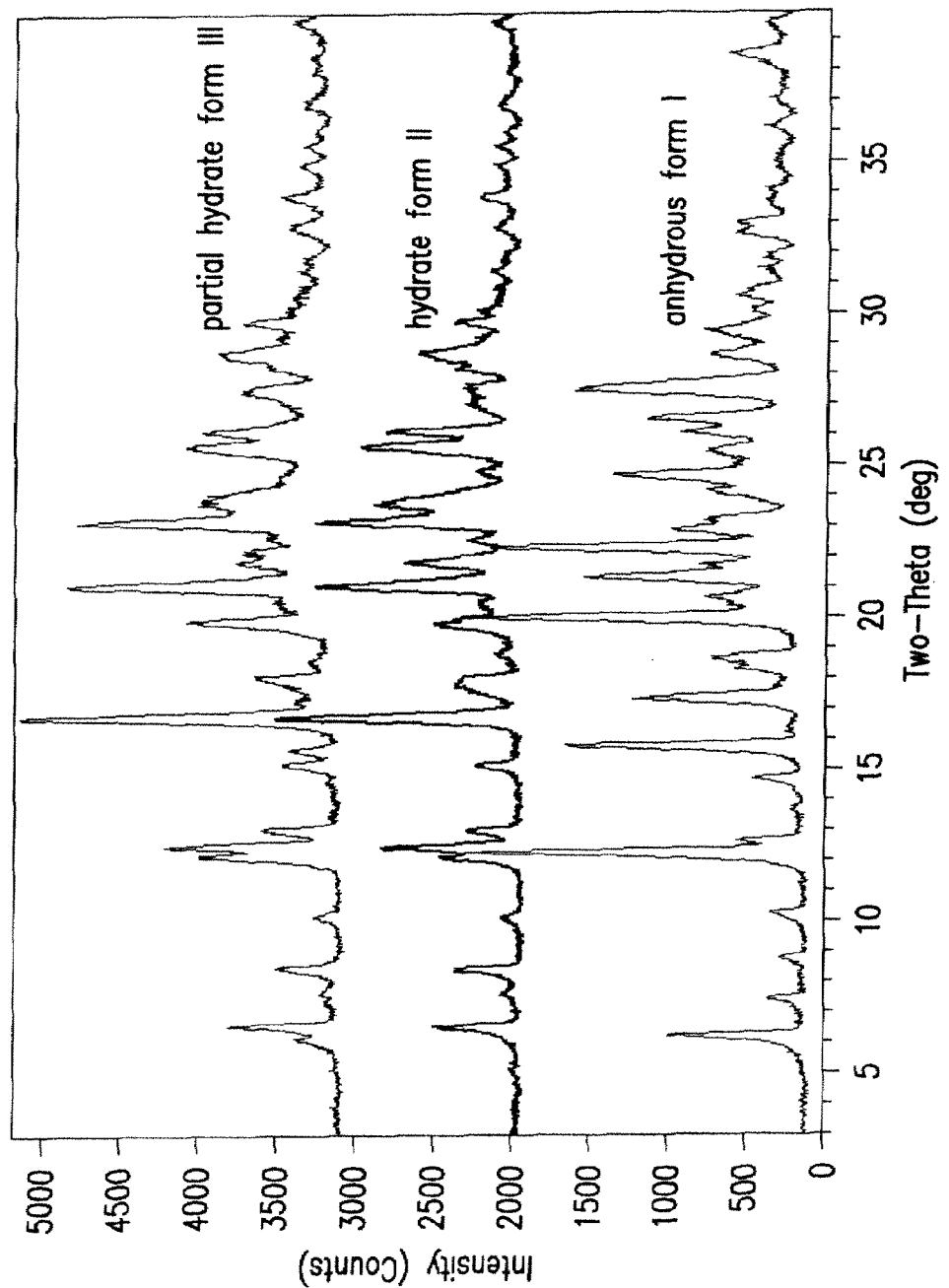
FIG. 5. XRD scans of Forms I, II and III (partial hydrate form) after exposure of Form I to 75% relative humidity at an ambient temperature for 22 days.

FIG. 5 includes an XRD scan of each of anhydrous Form I, monohydrate Form II and partial hydrate Form III of (E)-N-{4-[3-chloro-4-(2-pyridinylmethoxy)anilino]-3-cyano-7-ethoxy-6-quinolinyl}-4-(dimethylamino)-2-butenamide maleate after exposure of the anhydrous form of the maleate salt to a relative humidity of 75% at an ambient temperature of 20-25° C. for 22 days.

Figure 6:
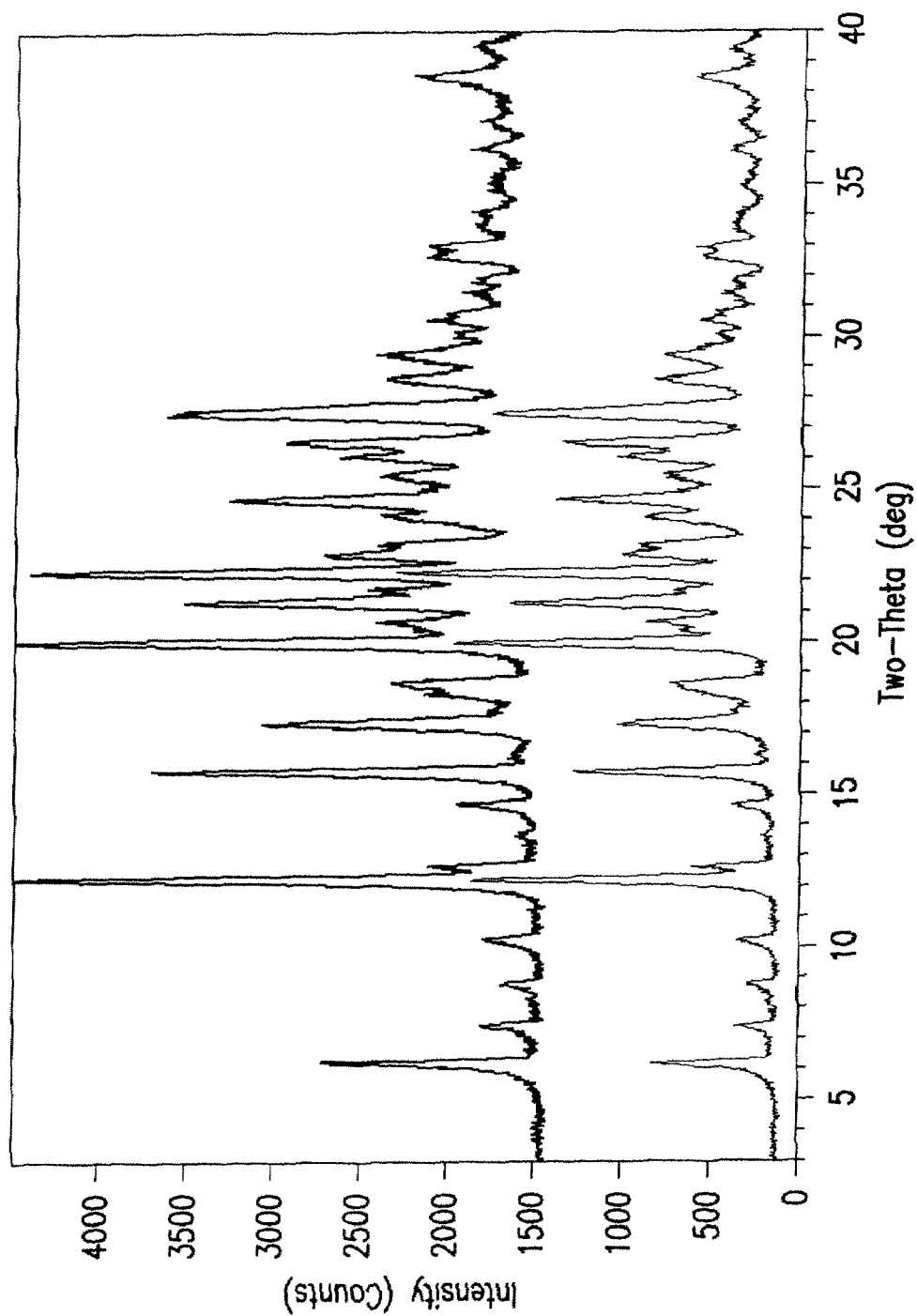
FIG. 6. XRD scans of two batches of Form I.
Figure 7:
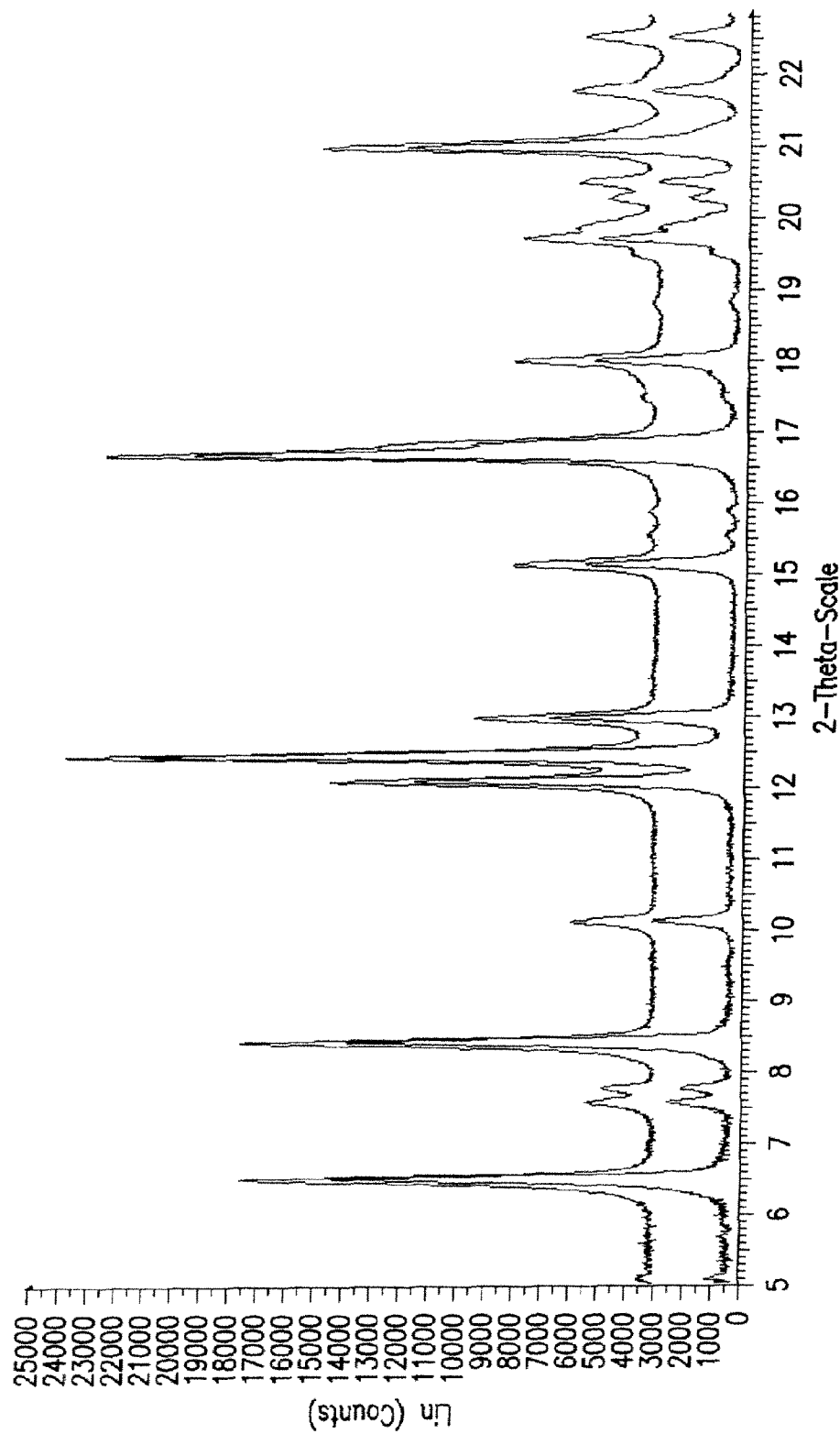
FIG. 7. XRD scans of Form II before and after exposure to a relative humidity of 50-60% at an ambient temperature of 20-25° C. for 24 hours.

FIG. 6 is an XRD scan of two batches of crystalline (E)-N-{4-[3-chloro-4-(2-pyridinylmethoxy)anilino]-3-cyano-7-ethoxy-6-quinolinyl}-4-(dimethylamino)-2-butenamide maleate in Form I. The anhydrous form of the maleate salt absorbs water and partially converts to the monohydrate form of the maleate salt at an ambient temperature of 20-25° C. over 24 hours. The monohydrate form of the maleate salt is relatively stable at an ambient temperature of 20-25° C. for 24 hours. FIG. 7 illustrates an XRD scan of crystalline (E)-N-{4-[3-chloro-4-(2-pyridinylmethoxy)anilino]-3-cyano-7-ethoxy-6-quinolinyl}-4-(dimethylamino)-2-butenamide maleate in Form II, before and after exposure to relative humidity of 50-60% at an ambient temperature of 20-25° C. for 24 hours. Exposing the monohydrate form of the maleate salt to higher temperatures (>50° C.) or heating under reduced pressure promotes water loss and full conversion back to the anhydrous form of the maleate salt.

Figure 8:
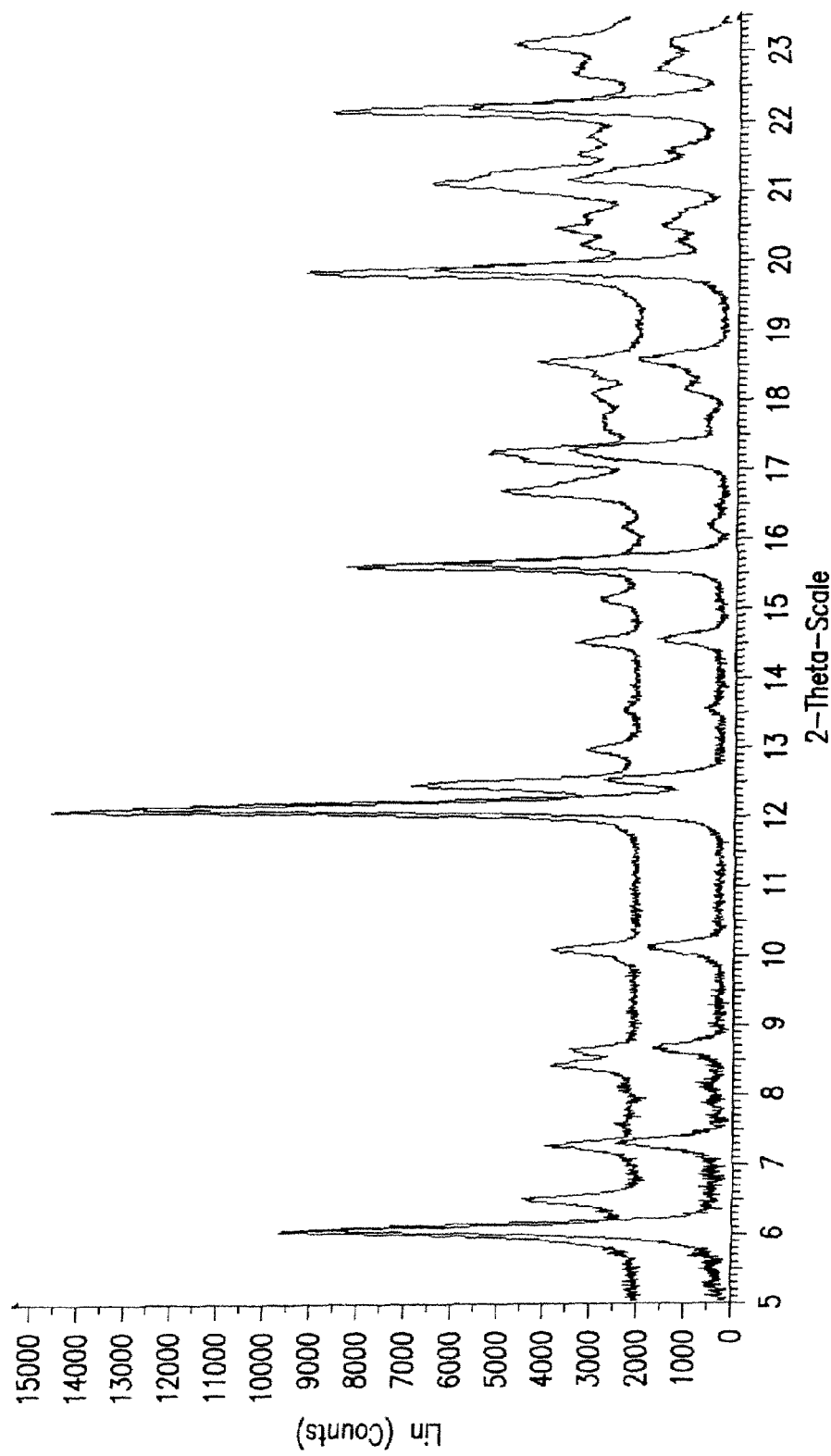
FIG. 8 XRD scans of Form I before and after exposure to relative humidity of 50-60% at an ambient temperature of 20-25° C. for 24 hours.

Form I, the anhydrous form, is readily converted to the monohydrate form, Form II. Form I can absorb water and convert partially to the monohydrate at a temperature of 20-25° C. and a relative humidity (RH) of 50-60% over time, as shown in FIG. 8. FIG. 8 is an XRD scan of crystalline (E)-N-{4-[3-chloro-4-(2-pyridinylmethoxy)anilino]-3-cyano-7-ethoxy-6-quinolinyl}-4-(dimethylamino)-2-butenamide maleate in Form I before (lower scan), and after (upper scan) exposure to relative humidity of 50-60% at room temperature of 20-25° C. for 24 hours. Hydrate peaks appear in the upper scan, indicating that the crystals absorb water under these conditions.

The stability of both forms of the maleate salt of (E)-N-{4-[3-chloro-4-(2-pyridinylmethoxy)anilino]-3-cyano-7-ethoxy-6-quinolinyl}-4-(dimethylamino)-2-butenamide was evaluated in closed and open containers at 40° C. and 75% RH. Both Form I and Form II remained stable for 6 months under these conditions. In the open containers, the anhydrous form of the maleate salt rapidly absorbed one mole of water to form the monohydrate form of the maleate salt. Samples in the closed containers remained dry. HPLC purity analysis indicated no significant increase in degradation products in both open and closed conditions for up to 6 months. The data is summarized in Table 5.

TABLE 5

SOLID STATE STABILITY OF THE ANHYDROUS MALEATE SALT (FORM I)

| | Closed Vial at 40° C./75% RH | | | | | Open Vial at 40° C./75% RH | | | | |
|---|---|---|---|---|---|---|---|---|---|---|
| Weeks in Storage | Potency as is (%) | Moisture (%) | Potency (dry basis) (%) | Major degradant (%) | Total impurities (%) | Potency as is (%) | Moisture (%) | Potency (dry basis) (%) | Major degradant (%) | Total impurities (%) |
| Initial | 100.50 | 0.35 | 100.85 | 0.23 | 0.57 | 100.50 | 0.35 | 100.85 | 0.23 | 0.57 |
| 1 | 100.07 | 0.39 | 100.46 | 0.23 | 0.57 | 99.13 | 2.82 | 102.01 | 0.22 | 0.55 |

TABLE 5-continued

SOLID STATE STABILITY OF THE ANHYDROUS MALEATE SALT (FORM I)

| | Closed Vial at 40° C./75% RH | | | | Open Vial at 40° C./75% RH | | | | |
|---|---|---|---|---|---|---|---|---|---|
| Weeks in Storage | Potency as is (%) | Moisture (%) | Potency (dry basis) (%) | Major degradant (%) | Total impurities (%) | Potency as is (%) | Moisture (%) | Potency (dry basis) (%) | Major degradant (%) | Total impurities (%) |
| 2 | 100.03 | 0.34 | 100.38 | 0.24 | 0.64 | 97.50 | 2.86 | 100.37 | 0.23 | 0.65 |
| 4 | 96.87 | 0.22 | 97.09 | 0.24 | 0.61 | 95.27 | 2.74 | 97.96 | 0.23 | 0.58 |
| 12 | 100.21 | 0.46 | 100.67 | 0.25 | 0.66 | 98.12 | 2.98 | 101.13 | 0.26 | 0.65 |
| 24 | 98.96 | 0.16 | 99.12 | 0.32 | 0.68 | 97.22 | 2.79 | 100.01 | 0.31 | 0.69 |

Reactive crystallization of the free base with maleic acid in different solvents was performed to determine which crystalline form(s) of the maleate salt resulted. Table 6 illustrates the results of the crystallization process in a mixture of n-propanol and water at various operating conditions. The wet cake in all experiments contains the monohydrate form of the maleate salt, which converts to the anhydrous form of the maleate salt after drying.

TABLE 6

REACTIVE CRYSTALLIZATION OF MALEATE SALT IN WATER/N-PROPANOL

| Exp # | T, ° C. | Conditions | Form, wet cake | Form, dry solid (50° C. and vacuum) |
|---|---|---|---|---|
| 1 | 25 | 10% water | Hydrate Form II | I + II (1 hr drying) |
| 2 | 45 | 10% water | Hydrate Form II | — |
| 3 | 60 | 10% water | Hydrate Form II | — |
| 4 | Variable | 5% excess acid + 10% water | Hydrate Form II | I + II (1 hr drying) |
| 5 | Variable | 10% excess acid + 10% water | Hydrate Form II | — |
| 6 | Variable | 20% excess acid + 10% water | Hydrate Form II | — |
| 7 | Variable | 15% water | Hydrate Form II | I + II (1 hr drying) |
| 8 | 25 | 13% water | Hydrate Form II | Anhydrous Form I (overnight drying) |
| 9 | 25 | 13% water | Hydrate Form II | — |
| 10 | 45 | 13% water | Hydrate Form II | — |
| 11 | 45 | 13% water | Hydrate Form II | — |
| 12 | 25 | 15% water | Hydrate Form II | — |
| 13 | 25 | 15% water | Hydrate Form II | Anhydrous Form I (overnight drying) |
| 14 | 45 | 15% water | Hydrate Form II | — |
| 15 | 45 | 15% water | Hydrate Form II | — |

Table 7 presents the results of reactive crystallization of the free base and maleic acid in various solvents, which resulted in anhydrous form of the maleate salt in all experiments.

TABLE 7

REACTIVE CRYSTALLIZATION OF MALEATE SALT IN VARIOUS SOLVENTS

| Exp # | T, ° C. | Solvent | Form, dry solid 50° C. and vacuum for 1 hr |
|---|---|---|---|
| 1 | Variable | Ethanol | Anhydrous Form I |
| 2 | Variable | Isopropanol | Anhydrous Form I |
| 3 | Variable | Ethyl acetate | Anhydrous Form I |
| 4 | Variable | Acetone | Anhydrous Form I |
| 5 | Variable | THF | Anhydrous Form I |
| 6 | Variable | Acetonitrile | Anhydrous Form I |
| 7 | Variable | Isopropyl acetate | Anhydrous Form I |

One solvent that appreciably dissolves the (E)-N-{4-[3-chloro-4-(2-pyridinylmethoxy)anilino]-3-cyano-7-ethoxy-6-quinolinyl}-4-(dimethylamino)-2-butenamide maleate salt is dimethylsulfoxide (DMSO). Cooling, anti-solvent and evaporative crystallization were performed in mixtures of DMSO and isopropanol or t-butyl methyl ether (tBME). The approach led to the decomposition of the solute in many cases. Anti-solvent and evaporative crystallization did not result in any new crystalline forms, as summarized in Tables 8 and 9.

TABLE 8

ANTI-SOLVENT CRYSTALLIZATION OF MALEATE SALT FORMS

| Exp # | T, ° C. | Solvent | | Form, wet cake |
|---|---|---|---|---|
| 1 | Salt dissolved in 5 vol. DMSO at T = 60° C. | 25 vol. IPA added at once | | Anhydrous Form I |
| 2 | Salt dissolved in 5 vol. DMSO at T = 60° C. | 20 vol. water added at once | | Hydrate Form II |
| 3 | Salt dissolved in 5 vol. DMSO at T = 60° C. | 2 vol. water and 25 vol. IPA added. Nucleated overnight | | Hydrate Form II |

TABLE 9

EVAPORATIVE CRYSTALLIZATION OF MALEATE SALT FORMS

| Exp # | Solvent | | Form, dry sample |
|---|---|---|---|
| 1 | DMSO:IPA | T = 50° C. vacuum | Anhydrous Form I |
| 2 | DMSO:IPA | T = 50° C. vacuum | Anhydrous Form I |
| 3 | DMSO:IPA | T = 50° C. vacuum | Anhydrous Form I |
| 4 | DMSO:IPA | T = 50° C. vacuum | Anhydrous Form I |

According to one embodiment, one way to convert anhydrous Form I into monohydrate Form II is by dissolving the salt into a solution of an organic solvent, for example such as THF, isopropanol (IPA), n-propanol, acetone, ethanol, methanol, and acetonitrile, and water, where in the water present is about 5% to about 20% by volume, though typically the water present is about 10% to about 15% by volume. This solution may be heated to increase solubility of the maleate salt; in one embodiment it is heated to about 45° C. or greater, in another embodiment it is heated to about 60° C. The solution is then allowed to sit for a period of hours to allow for crystallization, and the crystals are then filtered to give monohydrate Form II (see Table 6). In one embodiment the solution is allowed to sit for between about 12 and about 24 hours before filtration.

According to a separate embodiment, Form I is converted to Form II by re-slurrying it in organic solvent containing water and allowing the solution to stand exposed to the room temperature for several days, as shown in stability studies summarized in Table 10. This conversion will take place even in anhydrous solvents that have absorbed up to 1% water because anhydrous Form I readily absorbs moisture, as evidenced by FIG. 8. In one embodiment the re-slurry is allowed to stand for about 14 days.

TABLE 10

STABILITY OF CRYSTALLINE FORMS OF THE RESLURRY AT ROOM TEMPERATURE FOR 14 DAYS.

| Exp# * | Solvent | Initial Form | Final Form, wet cake |
|---|---|---|---|
| 1 | Ethanol | I | I |
| 2 | IPA | I | I |
| 3 | Ethyl acetate | I | I + some II |
| 4 | Acetone | I | I |
| 5 | THF | I | II |
| 6 | Acetonitrile | I | I |
| 7 | Methanol | I | I |
| 8 | Water | I | II |
| 9 | DMSO:IPA(1:1) | I | I |
| 10 | Ethanol | II | II |
| 11 | IPA | II | II |
| 12 | Ethyl acetate | II | II |
| 13 | Acetone | II | II |
| 14 | THF | II | II |
| 15 | Acetonitrile | II | II |
| 16 | Methanol | II | I |
| 17 | DMSO:IPA(1:1) | II | I |

The present invention is also directed to compounds associated with the free base or the maleate salt of (E)-N-{4-[3-chloro-4-(2-pyridinylmethoxy)anilino]-3-cyano-7-ethoxy-6-quinolinyl}-4-(dimethylamino)-2-butenamide, or the methods of this invention. One or more of these associated compounds may be found in the cooled solution in a process of this invention. Since these compounds may not be separated from the maleate salt, a pharmaceutical formulation prepared with the maleate salt may contain one or more of these compounds.

Formulations of the maleate salt were prepared and stored in 40° C./75% RH stability chambers for six months and in a 56° C. oven for one month. Samples were periodically pulled for testing. Samples were dissolved in 50/50 volume/volume acetonitrile/water with a concentration at about 0.5 mg/mL. The solutions were assayed directly using LC/MS methodology to identify any degradation products and impurities (referred to herein as associated compounds) at six-months. Structures of the associated compounds, detected by LC/MS are listed in Table 11. Notably, the amount of the degradation product associated with (E)-N-{4-[3-chloro-4-(2-pyridinylmethoxy)anilino]-3-cyano-7-ethoxy-6-quinolinyl}-4-(dim-ethylamino)-2-butenamide maleate is reduced by the production method of the present invention.

TABLE 11

STRUCTURES OF DEGRADATION PRODUCT AND PROCESS IMPURITIES

Process Impurity A

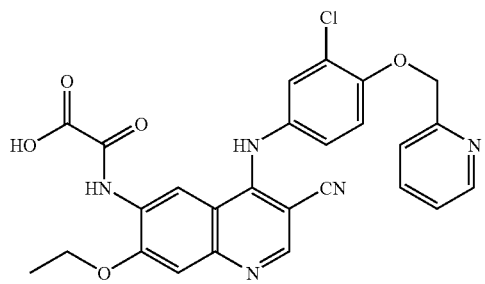

2-({4-[3-chloro-4-(2-pyridinylmethoxy)anilino]-3-cyano-7-ethoxy-6-quinolinyl}amino)-2-oxoacetic acid Exact Mass: 517.12

Process Impurity B

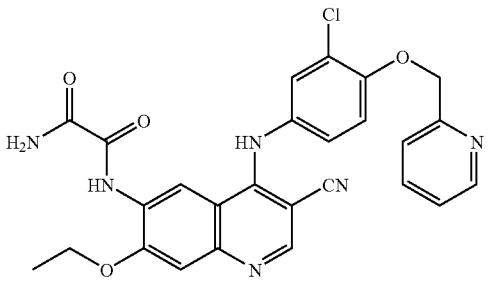

N$^1$-{4-[3-chloro-4-(2-pyridinylmethoxy)anilino]-3-cyano-7-ethoxy-6-quinolinyl}-ethanediamide Exact Mass: 516.13

Process Impurity C

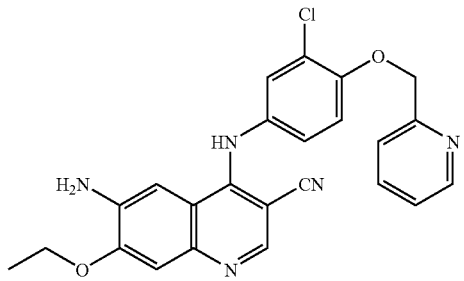

6-amino-4-[3-chloro-4-(2-pyridinylmethoxy)anilino]-7-ethoxy-3-quinolinecarbonitrile Exact Mass: 445.13

TABLE 11-continued

STRUCTURES OF DEGRADATION PRODUCT AND PROCESS IMPURITIES

Degradation Product A

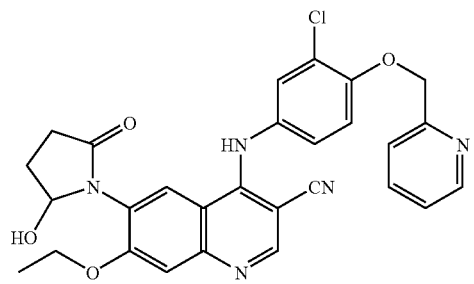

4-[3-chloro-4-(2-pyridinylmethoxy)anilino]-7-ethoxy-6-(2-hydroxy-5-oxopyrrolidinyl)-3-quinolinecarbonitrile
Exact Mass: 529.15

Process Impurity D

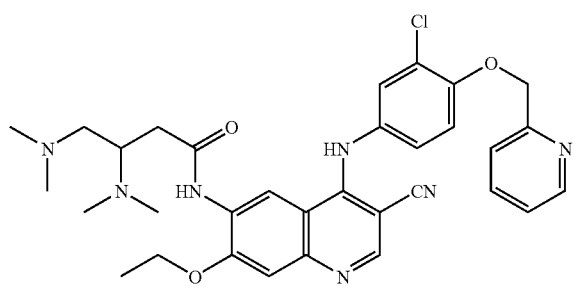

N-{4-[3-chloro-4-(2-pyridinylmethoxy)anilino]-3-cyano-7-ethoxy-6-quinolinyl}-3,4-bis(dimethylamino)butanamide
Exact Mass: 601.26

Process Impurity E

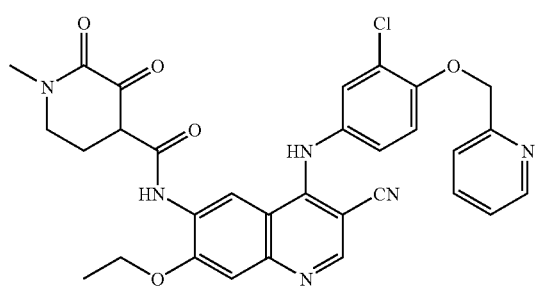

N-{4-[3-chloro-4-(2-pyridinylmethoxy)anilino]-3-cyano-7-ethoxy-6-quinolinyl}-1-methyl-2,3-dioxo-4-piperidinecarboxamide
Exact Mass: 598.17

TABLE 11-continued

STRUCTURES OF DEGRADATION PRODUCT AND PROCESS IMPURITIES

Process Impurity F

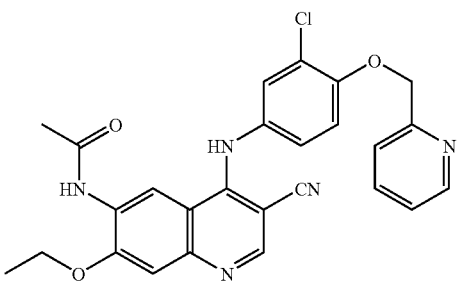

N-{4-[3-chloro-4-(2-pyridinylmethoxy)anilino]-3-cyano-7-ethoxy-6-quinolinyl}acetamide
Exact Mass: 487.14

Process Impurity G

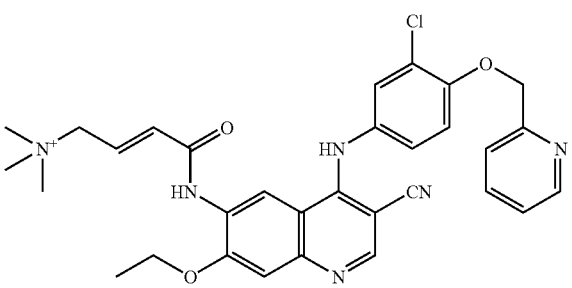

(E)-4-({4-[3-chloro-4-(2-pyridinylmethoxy)anilino]-3-cyano-7-ethoxy-6-quinolinyl}amino)-N,N,N-trimethyl-4-oxo-2-buten-1-aminium
Exact Mass: 571.22

Process Impurity H

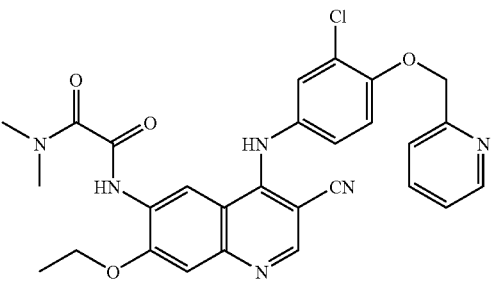

$N^1$-{4-[3-chloro-4-(2-pyridinylmethoxy)anilino]-3-cyano-7-ethoxy-6-quinolinyl}-$N^2$,$N^2$-dimethylethanediamide
Exact Mass: 544.16

TABLE 11-continued

STRUCTURES OF DEGRADATION PRODUCT AND PROCESS IMPURITIES

Process Impurity I

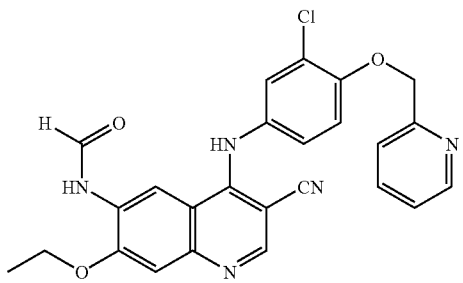

4-[3-chloro-4-(2-pyridinylmethoxy)anilino]-3-cyano-7-ethoxy-6-quinolinylformamide
Exact Mass: 473.13

Process Impurity J

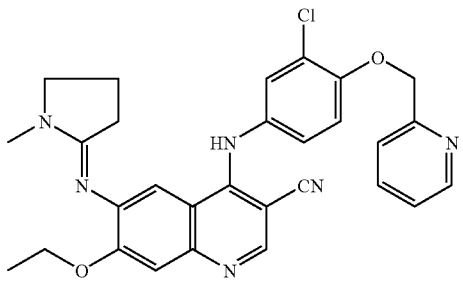

4-[3-chloro-4-(2-pyridinylmethoxy)anilino]-7-ethoxy-6-[(1-methyl-2-pyrrolidinylidene)amino]-3-quinolinecarbonitrile
Exact Mass: 526.19

The names of these associated compounds are:
2-({4-[3-chloro-4-(2-pyridinylmethoxy)anilino]-3-cyano-7-ethoxy-6-quinolinyl}amino)-2-oxoacetic acid;
$N^1$-{4-[3-chloro-4-(2-pyridinylmethoxy)anilino]-3-cyano-7-ethoxy-6-quinolinyl}-ethanediamide;
6-amino-4-[3-chloro-4-(2-pyridinylmethoxy)anilino]-7-ethoxy-3-quinolinecarbonitrile;
4-[3-chloro-4-(2-pyridinylmethoxy)anilino]-7-ethoxy-6-(2-hydroxy-5-oxopyrrolidinyl)-3-quinolinecarbonitrile;
N-{4-[3-chloro-4-(2-pyridinylmethoxy)anilino]-3-cyano-7-ethoxy-6-quinolinyl}-3,4-bis(dimethylamino)butanamide;
N-{4-[3-chloro-4-(2-pyridinylmethoxy)anilino]-3-cyano-7-ethoxy-6-quinolinyl}-1-methyl-2,3-dioxo-4-piperidinecarboxamide;
N-{4-[3-chloro-4-(2-pyridinylmethoxy)anilino]-3-cyano-7-ethoxy-6-quinolinyl}acetamide;
(E)-4-({4-[3-chloro-4-(2-pyridinylmethoxy)anilino]-3-cyano-7-ethoxy-6-quinolinyl}amino)-N,N,N-trimethyl-4-oxo-2-buten-1-aminium
$N^1$-{4-[3-chloro-4-(2-pyridinylmethoxy)anilino]-3-cyano-7-ethoxy-6-quinolinyl}-$N^2$, $N^2$-dimethylethanediamide;
4-[3-chloro-4-(2-pyridinylmethoxy)anilino]-3-cyano-7-ethoxy-6-quinolinylformamide; and,
4-[3-chloro-4-(2-pyridinylmethoxy)anilino]-7-ethoxy-6-[(1-methyl-2-pyrrolidinylidene)amino]-3-quinolinecarbonitrile.

Crystalline forms of the maleate salts of the present invention are useful for preventing, treating, or inhibiting inflammation or cancer by administering a therapeutically-effective amount of (E)-N-{4-[3-chloro-4-(2-pyridinylmethoxy)anilino]-3-cyano-7-ethoxy-6-quinolinyl}-4-(dimethylamino)-2-butenamide maleate to a subject. The subject may be a mammal, and more specifically, a human. The maleate salt may be administered in its anhydrous form, monohydrate form or partially hydrated form. One or more of the associated compounds discussed above may also be administered during this method.

Crystalline forms of the maleate salts of the present invention are useful for preparing pharmaceutical compositions for the inhibition of HER-2 kinase activity, which is linked to the treatment of cancer. The formulations contain a therapeutically effective amount of (E)-N-{4-[3-chloro-4-(2-pyridinylmethoxy)anilino]-3-cyano-7-ethoxy-6-quinolinyl}-4-(dimethylamino)-2-butenamide maleate and a pharmaceutically acceptable carrier. The pharmaceutical composition may be administered in its anhydrous form, monohydrate form or partially hydrated form. One or more of the associated compounds discussed above may also be administered during this method.

Pharmaceutical compositions and formulations of the present invention may be useful in the treatment of one or more of breast cancer, ovarian cancer, epidermoid tumors, colon cancer, prostate cancer, kidney cancer, bladder cancer, larynx cancer, esophagus cancer, stomach cancer, and lung cancer. According to one embodiment, the maleate salt is particularly useful in the treatment of breast cancer and/or ovarian cancer.

The pharmaceutical compositions and formulations including maleate salt forms of the invention may be administered orally, by intralesional, intraperitoneal, intramuscular or intravenous injection; infusion; liposome-mediated delivery; topical, nasal, anal, vaginal, sublingual, uretheral, transdermal, intrathecal, ocular or otic delivery. One mode of administration for the compound of the invention is the unit dose form. Suitable unit dose forms include tablets, capsules and powders in sachets or vials. The crystalline compounds of the present invention can be administered orally. Such compounds may be administered from 1 to 6 times a day, more usually from 1 to 4 times a day. The effective amount will be known to one of skill in the art; it may also be dependent upon the form of the compound, the mode of administration and the severity of the condition being treated. One of skill in the art could routinely perform empirical activity tests to determine the bioactivity of the compound in bioassays and thus determine what dosage to administer. However, in general, satisfactory results can be obtained with compounds of the present invention when dosed daily in the range of about 0.5 mg/kg to about 1000 mg/kg of body weight, but usually the effective dosage amount is between about 1 mg/kg to about 300 mg/kg per day.

The crystalline forms of maleate salts of the invention may be formulated with conventional excipients, such as fillers, disintegrating agents, binders, lubricants, flavoring agents, color additives, and carriers. The carrier may be a diluent, an aerosol, a topical carrier, an aqueous solution, a nonaqueous solution or a solid. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

If administered orally or topically, the crystalline forms of maleate salts of the invention may be provided to a subject in different carriers. Typically, such carriers contain excipients such as starch, milk, sugar, certain types of clay, gelatin, stearic acid, talc, vegetable fats or oils, gums, or glycols. Specific carriers are typically selected based upon the desired method of delivery, for example, phosphate buffered saline (PBS) could be used for intravenous or systemic delivery and vegetable fats, creams, salves, ointments or gels may be used for topical delivery.

The crystalline forms of maleate salts of the present invention may be delivered together with suitable diluents, preservatives, solubilizers, emulsifiers, adjuvants and/or carriers useful in treatment, inhibition or prevention of neoplasm. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN™ 20, TWEEN™ 80, PLURONIC™ F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, microemulsions, micelles, unilamellar or multilamellar vesicles, erythrocyte ghosts, or spheroblasts. Such compositions will influence the physical state, solubility, stability, rate of in vivo release, and rate of in-vivo clearance of the compound or composition. The choice of compositions will depend on the physical and chemical properties of the compound.

The crystalline forms of maleate salts of the invention also may be delivered locally via a capsule that allows a sustained release of the compound over a period of time. Controlled or sustained release compositions include formulations in lipophilic depots (for example, fatty acids, waxes, oils).

The crystalline forms of maleate salts of the invention can also be dosed with other active compounds that would be of benefit to a patient suffering from cancer, for example, other chemo agents or anti-biotics, or in conjunction with radiation therapy. These active compounds can be dosed with the compounds of the present invention simultaneously or in sequence. The compounds of the present invention can also be formulated to include the other active compound in the same dosage unit, for example both could be contained within one pill, table or capsule. Some of the possible types of active compounds that the compounds of the present invention could be used in combination with are mitotic inhibitors, such as taxol and vinblastine, alylating agents, such as cisplatin and cyclophosamide, antimetabolites, such as 5-fluorouracil and hydroxyurea, DNA intercalators, such as adriamycin and bleomycin, topoisomerase inhibitors, such as etoposide and camptothecin, antiangiogenic agents, such as angiostatin, and antiestrogens, such as tamoxifen.

This invention will be more fully described in conjunction with the following specific examples, which should not to be construed as limiting the scope of this invention. A skilled artisan will be able to re-arrange, combine, modify, or eliminate steps in the exemplified process, depending on process parameters and equipment.

EXAMPLE 1

Preparation of (E)-N-{4-[3-chloro-4-(2-pyridinylmethoxy)anilino]-3-cyano-7-ethoxy-6-quinolinyl}-4-(dimethylamino)-2-butenamide Maleate, Form II Crude (E)-N-{4-[3-chloro-4-(2-pyridinylmethoxy)anilino]-3-cyano-7-ethoxy-6-quinolinyl}-4-(dimethylamino)-2-butenamide free base (0.100 kg, 0.159 mole) is rinsed with a 10% solution of USP purified water in n-propanol (0.082 kg, 0.10 L) followed by the addition of water:n-propanol solution (0.74 kg, 0.90 L). Maleic acid is added (0.0191 kg, 0.164 mole) and the mixture is rinsed with 10% water:n-propanol (0.082 kg, 0.10 L). The mixture is quickly heated to 50-60° C. and held for a minimum of 15 min. until a solution is obtained. The hot solution is clarified through a pre-heated 50-60° C., 0.2 Mm filter cartridge and the filtrates are collected in a preheated 45-55° C., 2 L multi-neck flask. The filter cartridge is rinsed through with 10% water:n-propanol pre-heated to 45-55° C. (0.082 kg, 0.10 L). The solution is cooled over at least one hour to 40° C. and held at that temperature for 12 hours then cooled to room temperature (25° C.) over a minimum of four hours and held at that temperature for at least two hours. The mixture is filtered on a 12.5 cm diameter Buchner funnel for 5 min., then rinsed and washed with pre-filtered 10% water:n-propanol solution (2×0.12 kg, 2×0.15 L). The cake is dammed and suction maintained until dripping essentially stops, about 1 h.

EXAMPLE 2

Preparation of (E)-N-{4-[3-Chloro-4-(2-pyridinylmethoxy)anilino]-3-cyano-7-ethoxy-6-quinolinyl}-4-(dimethylamino)-2-butenamide Maleate, Form I The product from Example 1 (Form II) is dried (50° C., 10 mm Hg, 24 h) to give 94.4 g (88% yield) of crystalline, anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) (88% yield) with strength 80.8% (free base), 17.4% (maleic acid), total impurities 1.06%, largest single impurity 0.38%.

The invention claimed is:

1. An isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate, characterized by X-ray diffraction peaks at the following angles)(±0.20°) of 2θ in its X-ray diffraction pattern: 6.53, 8.43, 10.16, 12.19, 12.47, 13.01, 15.17, 16.76, 17.95, 19.86, 21.11, 21.88, 23.22, 23.78, 25.69, 26.17, 27.06, 27.58, 28.26, 28.73, and 29.77.

2. An isolated crystalline form according to claim 1 having substantially the X-ray diffraction pattern as shown in FIG. 7.

3. An isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate, characterized by X-ray diffraction peaks at the following angles)(±)0.20°) of 2θ in its X-ray diffraction pattern: 6.53, 8.43, 13.01, 15.17, 16.76.

4. An isolated crystalline form according to claim 3 having substantially the X-ray diffraction pattern as shown in FIG. 7.

* * * * *